United States Patent [19]

La Rochelle

[11] 4,157,386
[45] Jun. 5, 1979

[54] SOFT, CHEWABLE LOZENGE FORMING A STICKY COATING ON TEETH WHEN COMBINED WITH SALIVA IN THE MOUTH WHICH IS REMOVABLE ONLY BY BRUSHING

[76] Inventor: Paul J. La Rochelle, 427 Beech St., Holyoke, Mass. 01040

[21] Appl. No.: 907,167

[22] Filed: May 18, 1978

[51] Int. Cl.² ............................................. A61K 7/18
[52] U.S. Cl. ..................................... 424/52; 424/48; 424/49
[58] Field of Search ................................... 424/48–58

[56] References Cited
U.S. PATENT DOCUMENTS

| | | | |
|---|---|---|---|
| 2,449,184 | 9/1948 | Strean | 424/52 |
| 3,029,187 | 4/1962 | Steinhardt | 424/52 |
| 3,342,687 | 9/1967 | Gould | 424/52 |
| 3,431,339 | 3/1969 | Gyarmathy et al. | 424/52 |
| 3,914,434 | 10/1975 | Bohni | 424/49 X |

OTHER PUBLICATIONS

Muhlemann "Zuckerfreie Zahnschonende und Nicht-kariogene Bonbons und süssigkeiten" Schweizerische Monatsschrift für Zahnheilkunde 79:117–145, Feb. 1969.

*Primary Examiner*—Shep K. Rose
*Attorney, Agent, or Firm*—Abraham A. Saffitz

[57] ABSTRACT

A soft, chewable lozenge delivering to the mouth a solid unit package comprising a fluoride ion source, a starch adhesive, a polishing agent, a non-cariogenic sweetener in a minimum amount of water for solution such as xylitol or a non-cariogenic sweetener without water such as lycasin, a flavoring agent, if desired, and a combined viscosity builder/softening agent such as vegetable oil, all of which interact with saliva on chewing to coat the surfaces of the teeth, particularly interproximal surfaces, with a sticky mass removable only by brushing with a toothbrush. Chewing of this lozenge aids in incorporating the sticky mass in lingual interdental areas frequently not touched by brushing, especially when one is in a hurry, thereby assuring extra care in brushing to remove. Thus, brushing habits are improved for both adults and children. The unit package of saliva saturated paste thus applied by the lozenge insures adequate dosing for cleaning.

The long shelf storage stability of the lozenge assures easy dispensing. The size permits packing of the lozenge in a roll or small box in travel kits and medicine chests and the packaged product is handily dispensed at hotels, motels or travel terminals as a superior alternative to conventional toothpaste.

9 Claims, No Drawings

SOFT, CHEWABLE LOZENGE FORMING A STICKY COATING ON TEETH WHEN COMBINED WITH SALIVA IN THE MOUTH WHICH IS REMOVABLE ONLY BY BRUSHING

BACKGROUND OF THE INVENTION

FIELD OF THE INVENTION

This invention lies in the field of unit packaged dental preparations in soft and sweetened lozenge form designed to be chewed and not ingested for delivering to the hard to reach interproximal areas of the teeth the lozenge material coverted by saliva into a pasty sticky mass adhering to the teeth which is removable only by brushing.

MOTIVATION FOR THE INVENTION

In dealing with children daily in the practice of dentistry I, the inventor, most often am asked what kind of toothpaste is best and why do our children get so many cavities even with brushing.

I feel that it is definitely not the toothpaste as much as the amount and type of brushing which causes a problem. As to why so much decay, I reply that brushing must be done properly to be effective. Children frequently put toothpaste on the labial surfaces of the front and side teeth but these are not the parts of the teeth that require the most brushing.

I asked myself why not create a product that sticks in the crevices of the teeth, makes children brush harder, gets the teeth cleaner, and the taste of which would be enjoyed during brushing.

Thus the present invention was developed to meet the above requirement of motivation for proper brushing at the proper times. As stated in "Relevance of Biomedical Engineering to Dentistry", Publication Number NIH 77-1198, Feb. 2-4, 1976, pages 174 and 175, U.S. Department of Health, Education and Welfare:

"Currently dental plaque can be removed by such simple mechanical means as the toothbrush, wood point or dental floss. But it remains difficult to motivate people even to brush their teeth. If more could be persuaded to do so, the results would have substantial clinical application. ...".

To attempt to achieve the above motivation I conceived of the soft, sweetened lozenge which, by combining with saliva in the mouth, forms a sticky coating on the teeth which can be removed only by proper brushing.

The basic ingredients making up the soft, chewable lozenge are a finely divided polishing agent, a dry fluoride ion source, a starch adhesive, a softening agent functioning as a viscosity builder, a non-glycogenic, non-cariogenic sweetener with enough water or glycerin to dissolve the sweetener, and a flavoring agent, if desired. These ingredients are stable, after mixing, because they are substantially dry. They provide effective concentrations of fluoride in available form. Such effective amounts of fluoride in available form are often difficult to stabilize in ordinary toothpaste due to the higher water content of toothpaste. Further, the control of fluoride in available form in tooth powder is difficult because a low critical amount is required in ionic form and overdosage is frequent. Overdosage is extremely objectionable for a variety of reasons.

DESCRIPTION OF THE PRIOR ART

Candy coated chewing gum is widely available under the Trademark "Chiclets" but these have little cleaning capacity and because of the highly cohesive character of "Chiclets" there is no penetration of the interproximal areas of the teeth. Adding abrasive, as in "Dentyne" chewing gum, does not markedly change the cleaning capacity of the gum. However, like the present invention, there are examples of products which are not designed to be swallowed.

Medicinal tablets under the Trademark "Feenamint" are designed to make an otherwise unpleasant medicine more palatable but do not function to coat the teeth nor reside in the oral cavity. Like the "Chiclet", and the present invention, these also are not designed to be swallowed.

In Clark, U.S. Pat. No. 396,192, granted 1889, there is disclosed the basic teaching of either dry tooth powder or toothpaste using the same cleaning ingredients of soap, polishing agent, flavoring agent and sweetener (see page 1, column 2, lines 75 through 93). Clark either adds glycerine or deletes it to make a paste or powder respectively. In contrast, the invention uses only saliva to convert the solids in the lozenge to put paste onto the teeth.

Hay, U.S. Pat. No. 3,151,028, shows a tablet which is comprised of 94 parts sorbitol, 4 parts malic acid and 2 parts sodium chloride. The tablet in Example 1, column 6, lines 36 through 43, is compressed at 25 tons per square inch and is too hard to be crushed by the teeth. It takes approximately five minutes to dissolve the tablet in the mouth. There is no teaching of a soft, chewable tablet which is mixed and formed at low pressure which quickly picks up saliva to dissolve in the mouth and coat the teeth.

Emond, U.S. Pat. No. 3,116,208, shows a tablet which is easily crushed by the teeth and formed at about 1,600 pounds per square inch of pressure, a small fraction of the pressure of the Hay patent. The two components of the Emond tablet are calcium carbonate and sodium lauryl sulfate, both solids. The present tablet differs in being free from sulfate, in containing fluoride and in containing flavoring oils.

Bouchal, U.S. Pat. No. 3,531,564, is like Emond in combining a polishing agent with a detergent but the detergent differs from that of Emond. Bouchal is also of interest because he describes a fluoride as a desirable ingredient and further requires at least 10% to 10% glycerine for liquid binder (see column 3, lines 15 through 27). The fluoride which is used may be any one of the salts mentioned at lines 55 through 70, column 3. These include copper, lead and zinc.

Howell, U.S. Pat. No. 3,962,417, shows an effervescent tablet which is made with stannous fluoride, sodium lauryl sulfate, very high quantities of citric acid and which completely dissolves in the mouth. The claim in this patent is for the method of chewing the tablet and brushing the teeth after all of the ingredients have dissolved. The ingredients in the present invention do not dissolve.

Barth, U.S. Pat. No. 3,932,606, shows a chewable dental tablet having a composition equivalent to a dental cream without water. The tablet in Barth can be crushed into particles. There is no adhesive in the Barth tablet. In contrast, the ingredients in the present invention become an adhesive mass due to the action of saliva on the dry starch adhesive and polishing agent. This mass sticks to the interproximal areas of the teeth during the chewing rather than simply being crushed as in Barth. There is no concept of the tablets formulated with starch adhesive which will increase the need for longer brushing.

Forkner, U.S. Pat. No. 3,615,645, shows gums, pectins and starches for bakery mix, custard and the like, (see column 2, lines 15 through 23) but invert sugar or corn syrup must be present. Forkner also shows cereal flour (column 3, lines 60 through 75) which is mixed with vegetable or synthetic fat but states that stickiness must be prevented.

DISTINCTIONS OVER THE PRIOR ART

The present soft, sweet and potentially sticky, chewable lozenge for unit dentifrice delivery to the mouth where it is dispersed by the saliva to form insoluble starch adhesive containing fragments sticking to the teeth differs from the prior art compositions in:
(a) confining the leachable and water soluble ingredients to non-cariogenic and non-glycogenic sweeteners and flavoring agents whereby these are the only saliva leachable components of the lozenge;
(b) combining the insoluble polishing ingredients, the soluble flavoring ingredients and the viscosity builders or thickening agents with minimum liquid and/or water to form a soft and easily breakable lozenge delivering a predetermined quantity of insoluble polishing ingredient and inorganic fluoride in available ion form in an amount and form which will not dissolve in substantial amounts in the saliva to thereby provide only one avenue for removal of the sticky starch adhesive paste mixture, namely by brushing;
(c) combining the insoluble polishing agent in critical major proportion with starch adhesive in minor proportion, both in essentially dry form, and intimately comingling these dry solids by the sweetener; and
(d) introducing a softening agent functioning as a viscosity builder, making the lozenge soft, sweet and sticky on the teeth.

In contrast to Howell, U.S. Pat. No. 3,151,028, there is no reliance upon a hard tablet which slowly dissolves so that it must be held in the mouth for about five minutes to stimulate copious salivation and thereby furnish the aqueous dissolving medium for brushing. A wholly different physical action occurs in the invention under chewing forces to disperse starch adhesive containing pasty fragments in the mouth which deposit on the nearest available site, e.g., the hard to reach interproximal spaces, both labial and lingual, on the upper and lower teeth. Additionally, chewing forces are entirely different with a soft lozenge. If, in Howell, the brushing were to be omitted, there could be substituted therefor the step of simply rinsing or washing the mouth out with water. In contrast, in the invention, the adhesive paste sticks to the teeth, cannot be removed by rinsing, and is removed only by brushing. Thus in Howell brushing is elective while in the invention it is mandatory if the polishing agent is to be removed.

In contrast to Bouchal, U.S. Pat. No. 3,531,564, which requires a special detergent to stabilize fluoride, the detergent is eliminated and the remaining, substantially dry, ingredients stabilize the fluoride in the presence of the softening agent. The effectiveness is improved without the cost of an added chemical stabilizer by a totally different mechanism of physical mixing in the essentially dry state with potentially troublesome ingredients being eliminated, e.g., the added stabilizer having its own physiological action.

Forkner, U.S. Pat. No. 3,615,645, has an opposite teaching of preventing stickiness in a water wet sweetener-starch mixture. The present discovery that one-half of the starch amount used in Forkner is surprising indeed since one would not expect stickiness from this small amount of starch.

DISTINGUISHING THEORY OF OPERATION OVER THE PRIOR ART

The theory of operation which the inventor believes explanatory of the effective results achieved with the present soft, sweetened and potentially sticky composition is based upon the observation that starch adhesive can be effective with non-cariogenic sweetener to make non-sticky cleaner-polisher become sticky when wet with the saliva in the mouth. The surprising discovery is that the development of stickiness due to the starch adhesive occurs almost immediately as the soft particles are broken by the teeth and travel to the interproximal areas of the teeth.

The polysaccharides in the non-cariogenic sweetener group and the starch group cooperate in a unique way by their sharing of limited amounts of water in the present formulation totally contrary to the principles of operation in the prior art of food and dessert preparation exemplified by Forkner or in the prior art of toothpaste or toothpowder.

The rate of development of sweet taste in the mouth requires that the non-cariogenic sweetener be predissolved if instantaneous sweetness is the goal. Instantaneous sweetness is a primary objective of the invention.

The starch adhesive is activated by the small amount of water present in lycasin, xylitol or sorbitol, or mixtures thereof in any combination. Lycasin, a commercially available mixture of sorbitol, maltitol and high molecular weight dextrans, contains about 30% water. This amount of water in lycasin is the smallest amount of water contained by the three primary sweeteners lycasin, xylitol or sorbitol.

The cleaner-polishers are all inherently hydrophilic and, remarkably, the two carbohydrate components, sweetener and starch adhesive, appear to permit a degree of coating of the cleaner-polisher particles, this coating being enhanced by the use of conventional dispersing agents, preferably non-ionic agents, and lumpiness is eliminated during preparation of the lozenge by the use of vegetable oil, preferably unsaturated vegetable oil.

The common adhesive properties of starch in aqueous dispersion, as, for example, saliva, are a well known characteristic which is used by the manufacturers to grade starch. See page 673, Volume 18, *Kirk-Othmer Encyclopedia of Chemical Technology*, Second Edition, copyright 1969, Interscience Publisher. The starches so characterized for the food market are from wheat, potato, corn, sorghum, rice and high amylose-corn. The present example of corn starch is merely illustrative of a readily available form.

OBJECTS OF THE INVENTION

An object of the invention is to provide a chewable lozenge containing a small amount of starch adhesive, a large amount of cleaning-polishing agent, non-cariogenic sweetener and flavoring and coloring agents, if desired, which react with the saliva in the mouth on chewing to coat the surfaces of the teeth with a sticky mass which cannot be removed by simply washing out with water but must be brushed with a toothbrush.

Another object of the invention is to provide a chewable lozenge as in the preceeding paragraph but adding a fluoride ion source in precise unit dosage form to the lozenge.

Still another object of the invention is to provide a chewable lozenge without the added fluoride ion source.

A further object of the invention is to provide a unit package of essentially dry ingredients, except for the non-cariogenic sweetener, to provide a soft product resembling a confection and producing instantaneous sweetness in the mouth, such as a mint, but which, when chewed, forms a sticky mass adhering to the interproximal surfaces of the teeth necessitating brushing for removal.

Yet another object of the invention is to provide a method of cleaning the teeth which involves chewing a unit package or lozenge which is in a soft physical form but not a toothpaste and not a tooth powder.

Other and further objects of the invention will become apparent from the following examples and detailed description of the preferred embodiments.

SUMMARY OF THE INVENTION

A soft chewable dentifrice composition which is not a paste and not a powder comprises:

|  | Choice | Range | Preferred |
|---|---|---|---|
| Non-Cariogenic Sweetener | Xylitol | 40–30 | 36 |
| Flavor | Oil of Orange | 0.1 | G.S. |
| Color | Orange U.S. Certified | 0.05 | G.S. |
| Cleaner-Polisher | Hydrated Alumina | 50–30 | 40 |
| Non-Ionic Dispersing Agent | Mono-Methylether Polyethylene Glycol 600 | 3–0.5 | 2 |
| Liquid Dispersing Agents | Lecithin | 5–1 | 2 |
|  | Glycerin | 2–0.5 | 2 |
| Starch Adhesive | Corn Starch | 10.5 | 5 |
| Viscosity Builder | Unsaturated Vegetable Oil | 20–5 | 10 |
| Antioxidants | Methyl Parasept | 0.1–0.3 | 0.17 |
|  | Propyl Parasept | 0.01–0.1 | 0.02 |
| Fluoride Ion Source | Sodium Fluoride | 0.05–0.3 | 0.22 1000 ppm as fluoride |

The fluoride ion source is optional. Certain parts of the country permit its use, others do not. Although an important advantage of the invention is the stability and precise dosing of fluoride, the main inventive concept of soft and potentially sticky coating ingredients is not dependent upon this fluoride ion advantage.

DESCRIPTION OF THE PREFERRED EMBODIMENTS

EXAMPLES 1 THROUGH 10

The following table provides a range of compositions prepared from the ingredients which are mixed to produce the compositions in substantially dry form. From the separate examples the unit lozenge of the invention is prepared.

Each column, 1, 2, 3 . . . 10, represents parts by weight and the essential ingredients, except for fluoride, flavor, color and antioxidant, total approximately 100. Fluoride is at about 1,000 ppm or about 0.2 pph of mixture.

The xylitol or xylitol-sorbitol mixtures are employed in solution. The amount of water gives about an 8% to 10% xylitol solution and a 22% sorbitol solution. These solutions, when added to the cleaner polisher, starch adhesive and vegetable oil form a soft, substantially dry composition made slightly sticky by the starch adhesive. The cleaner polisher strongly absorbs the water of the sweetener because of the inherent hydrophilic property of the selected dental cleaner polisher.

The lycasin formulations in Examples 2, 4, 6 and 10 illustrate the use of a commercial formulation which consists essentially of a mixture of sorbitol, maltitol and high molecular weight dextrans which contains about 30% water in the form supplied by the manufacturer. In Examples 2, 4, 7 and 10 lycasin alone serves as non-cariogenic sweetener and these illustrate very low sweetener proportions over a wide range. Example 6 illustrates a lycasin-sorbitol mixture which combines the instant sweetness of lycasin with the economy of sorbitol. Obviously this Example 6 mixture represents a lycasin formulation with a larger amount of water.

Inspection of the Examples 1 through 10 in the Table 1 establishes that:

(a) the water content may be as low as 6% and as high as 35% for mixing purposes but is preferably at the lower end of the range when a dry lozenge is made;

(b) where higher amounts of water are used to aid in mixing, evaporation occurs so that the paste made by mixing can be simply dosed;

(c) the proportion of starch adhesive is surprisingly low;

(d) the ingredient in largest proportion, e.g., in major amount, is the cleaner-polisher which exhibits for all of the illustrative embodiments of the Examples a hydrophilic characteristic to provide proper mixing characteristics and a high cleaning and polishing action to conform with American dental standards;

(e) the proportion of unsaturated vegetable oil is surprisingly low; and (f) the essential physical characteristics of the lozenge composition, not a paste and not a powder, are independent of the presence or absence of fluoride ion source.

All of the examples listed in Table 1 contain a fluoride ion source but this may be omitted as shown in Example 11 which follows Table 1.

| TABLE 1, PART A. | EXAMPLES 1 THROUGH 10 | | | | | | | | | |
|---|---|---|---|---|---|---|---|---|---|---|
|  | 1 | 2 | 3 | 4 | 5 | 6 | 7 | 8 | 9 | 10 |
| NON-CARIOGENIC SWEETENER: | | | | | | | | | | |
| Xylitol 8% aqueous | 36 |  | 22 |  | 40 |  |  | 20 | 8 |  |
| Lycasin |  | 36 |  | 22 |  | 8 | 20 |  |  | 20 |

-continued

EXAMPLES 1 THROUGH 10

| | 1 | 2 | 3 | 4 | 5 | 6 | 7 | 8 | 9 | 10 |
|---|---|---|---|---|---|---|---|---|---|---|
| Sorbitol 22% aqueous | | | | | | | | | 22 | 22 |
| FLAVOR: | | | | | | | | | | |
| Oil of Orange | 0.1 | | | | | | | | | |
| Oil of Peppermint | | | | | | | | | | |
| Oil of Wintergreen | | | | | | | | | | |
| CLEANER-POLISHER: | | | | | | | | | | |
| Aluminum Hydrate | 39 | 39 | | | | | | | | |
| Insoluble Calcium Metaphosphate | | | 50 | | | | | | | |
| Dicalcium Phosphate | | | | | 40 | | | | 37 | 47 |
| Calcium Pyrophosphate | | | | 50 | | | | | 7 | 7 |
| Silica | | | | | | 30 | | | | |
| Calcium Carbonate | | | | | | | 60 | 60 | | |
| Trimagnesium Phosphate | | | | | | | | | 7 | 7 |
| FLUORIDE ION SOURCE: | | | | | | | | | | |
| SnF$_2$ | | | 0.2 | 0.2 | | 0.2 | | | 0.2 | 0.2 |
| Sodium Fluorophosphate | 0.2 | 0.2 | | | | | | | | |
| Sodium Fluoride | | | | | 0.2 | | 0.2 | 0.2 | | |

TABLE I, PART B

| | 1 | 2 | 3 | 4 | 5 | 6 | 7 | 8 | 9 | 10 |
|---|---|---|---|---|---|---|---|---|---|---|
| NON-IONIC DISPERSING AGENT: | | | | | | | | | | |
| Mono-Methylether Polyethylene Glycol 600 | 2 | 2 | 3 | 3 | 0.5 | 0.5 | 2 | 2 | 3 | 3 |
| VISCOSITY BUILDER: | | | | | | | | | | |
| Unsaturated Vegetable Oil (corn or safflower oil) | 15 | 15 | 10 | 10 | | 15 | 15 | | | |
| STARCH ADHESIVE: | | | | | | | | | | |
| Corn Starch | 5 | 5 | 10 | 10 | 10 | 10 | 10 | 10 | 5 | 5 |
| LECITHIN | 2 | 2 | 3 | 3 | 5 | 5 | 3 | 3 | 3 | 3 |
| GLYCERIN | 1 | 1 | 2 | 2 | 4 | 4 | 5 | 5 | 5 | 5 |
| ANTIOXIDANT: | | | | | | | | | | |
| Methyl Parasept | 0.17 | 0.17 | 0.10 | 0.10 | 0.1 | 0.1 | 0.17 | 0.19 | | |
| Propyl Parasept | 0.026 | 0.026 | 0.03 | 0.03 | 0.02 | 0.02 | 0.03 | 0.03 | | |

In the foregoing formulation flavor and color can be modified to provide, for instance, orange for breakfast, mint for after dinner and any one of a variety of flavors after lunch, e.g., cinnamon or clove. The color would match the flavor, e.g., orange for the orange, certified red dye 40 for the cinnamon, green vegetable dye for the mint, etcetera.

Antioxidant serves to stabilize the vegetable oil softening agent and contributes to longer shelf storage life of the packaged lozenge.

The liquid dispersing agents, either lecithin or glycerin, exemplify additives which are optional to control, in conjunction with the viscosity builder, the softness of the lozenge and the possibility of hardening on storage. Their use is an advantage also where the lozenge might be exposed to very low humidity.

EXAMPLE 11

This example illustrates lozenges free of fluoride. Formulations as set out in Table 1 were prepared, except that the fluoride ion source was omitted. The lozenges formed by tabletting of the compositions of this example were identical in appearance and physical characteristics to the fluoride containing compositions of Examples 1 through 10 which were tabletted in the same manner.

PREFERRED TABLETTING SIZES

Conventional tabletting machinery is employed to form tablets of the substantially dry compositions of Examples 1 through 11 which may be square or round in shape. One desirable square size is a tablet about 2 cm × 2 cm having a height of about 0.7 cm and a weight of about 1 ounce.

A similar round lozenge has a diameter of about 2 cm and a height of about 0.7 cm.

OPTIONAL INGREDIENTS

Although a few typical flavoring and coloring agents are shown, flavoring agents such as in U.S. Pat. No. 4,071,614 granted May, 1977 or U.S. Pat. No. 3,957,964 granted May, 1976 may be used and approved dye stuffs or natural colors may be used. Special flavoring oils as in U.S. Pat. No. 3,957,964 may be used. Obviously, liquid oil of cinnamon, natural vanilla extract, natural orange oil, natural mint oil and the like may be used.

If a bacteriostat is preferred, such as well known ammonium bacteriostats used in mouthwash, it may also be added in an effective amount.

Such additions merely illustrate the adaptability of the new lozenge of the invention to meet various marketing requirements.

Having thus disclosed the invention I now claim:

1. A soft, chewable lozenge delivering to the mouth a composition forming a sticky coating on the teeth when combined with saliva and completely removable from the teeth only by brushing, said composition comprising:

a water-containing, non-cariogenic sweetener in an amount of about 20% to 36% by weight selected from the group consisting of xylitol, lycasin, mixtures of xylitol and sorbitol and mixtures of lycasin and sorbitol serving as the sole sweetening agent;

a cleaner-polisher for the teeth in an amount of from about 30% to 60% by weight, which is greater than the amount of said sweetener;

a starch adhesive in an amount of about 5% to 10% by weight; and a viscosity builder and softening agent comprising an unsaturated vegetable oil which physically softens the mixture of cleaner-polisher and sweetener while interacting physically with the starch adhesive to thicken the composition and enhance adhesion to the teeth.

2. A lozenge as claimed in claim 1 containing a fluoride ion source in an amount of about 0.2% by weight of said composition.

3. A lozenge as claimed in claim 2 including a flavoring agent.

4. A lozenge as claimed in claim 3 including a coloring agent.

5. A lozenge as claimed in claim 4 including a dispersing agent.

6. A lozenge as claimed in claim 5 wherein said dispersing agent is a non-ionic dispersing agent.

7. A lozenge as claimed in claim 5 wherein said dispersing agent includes lecithin.

8. A lozenge as claimed in claim 1 including an antioxidant in an amount effective to protect said unsaturated vegetable oil from oxidation during mixing and storage.

9. A composition forming a sticky coating on the teeth when combined with saliva in the mouth and completely removable from the teeth only by brushing, said composition comprising:

a water-containing, non-cariogenic sweetener in an amount of about 20% to 36% by weight selected from the group consisting of xylitol, lycasin, mixtures of xylitol and sorbitol and mixtures of lycasin and sorbitol serving as the sole sweetening agent;

a cleaner-polisher for the teeth in an amount of from about 30% to 60% by weight, which is greater than the amount of said sweetener;

a starch adhesive in an amount of about 5% to 10% by weight; and a viscosity builder and softening agent comprising an unsaturated vegetable oil which physically softens the mixture of cleaner-polisher and sweetener while interacting physically with the starch adhesive to thicken the composition and enhance adhesion to the teeth.

* * * * *